(12) United States Patent
Radziunas et al.

(10) Patent No.: US 8,529,613 B2
(45) Date of Patent: Sep. 10, 2013

(54) ADJUSTABLE THERMAL CAP

(75) Inventors: Jeffrey Radziunas, Wallingford, CT (US); Charles D. Lennox, Hudson, NH (US)

(73) Assignee: MedCool, Inc., Wellesley, MA (US)

( * ) Notice: Subject to any disclaimer, the term of this patent is extended or adjusted under 35 U.S.C. 154(b) by 1542 days.

(21) Appl. No.: 11/870,441

(22) Filed: Oct. 11, 2007

(65) Prior Publication Data

US 2008/0097560 A1   Apr. 24, 2008

Related U.S. Application Data

(60) Provisional application No. 60/852,600, filed on Oct. 18, 2006.

(51) Int. Cl.
*A61F 7/00* (2006.01)

(52) U.S. Cl.
USPC .......................... 607/110; 62/259.3

(58) Field of Classification Search
USPC .................. 607/104, 109, 110; 62/259.3
See application file for complete search history.

(56) References Cited

U.S. PATENT DOCUMENTS

| | | | |
|---|---|---|---|
| 26,663 A | 1/1860 | French | |
| 998,804 A | 7/1911 | Salisbury | |
| 2,043,721 A * | 6/1936 | Warwick | ............................ 34/90 |
| 2,224,876 A | 12/1940 | Matys | |
| 2,255,751 A | 9/1941 | Bancel | |
| 2,272,481 A | 2/1942 | Rinkes et al. | |
| 2,416,788 A | 3/1947 | Andrews | |
| 2,512,990 A | 6/1950 | Akerman | |
| 2,540,547 A | 2/1951 | Rodert | |
| 2,566,600 A | 9/1951 | Colon | |
| 2,706,988 A | 4/1955 | Weber | |
| 3,085,405 A | 4/1963 | Frantti | |
| 3,153,720 A | 10/1964 | Petronio et al. | |
| 3,229,681 A | 1/1966 | Gluckstein | |

(Continued)

FOREIGN PATENT DOCUMENTS

| | | |
|---|---|---|
| JP | 05220186 | 8/1993 |
| JP | 05220187 | 8/1993 |

(Continued)

OTHER PUBLICATIONS

Hachimi-Idrissi et al., "Mild Hypothermia Induced by a Helmet Device: A Clinical Feasibility Study," Resuscitation 51:275-281 (2001).
International Search Report from Intl. Appl. No. PCT/US03/13091, mailed Dec. 4, 2003.
International Search Report from Intl. Appl. No. PCT/US03/35930, mailed Jul. 1, 2004.
International Search Report from Intl. Appl. No. PCT/US04/24937, mailed Jul. 6, 2005.

(Continued)

*Primary Examiner* — Ralph Lewis
(74) *Attorney, Agent, or Firm* — Pepper Hamilton, LLP; Thomas Engellenner

(57) ABSTRACT

A thermal cap that can fit a variety of head sizes is disclosed. The cap can include a shell having a fluid inlet and outlet, a sealing mechanism and removable sizing layers disposed within the shell. Depending upon the size of a patient's head, sizing layers can either be added to or removed from the outer shell to maintain a fluid circulation space between the head and the rigid shell and allow substantially even distribution of a thermal fluid about the scalp of the patient during operation. The shell is preferably rigid and an elastomeric member can seal the periphery of the cap to the patient's head to prevent leakage. Other types and aspects of thermal cap systems are also disclosed.

8 Claims, 14 Drawing Sheets

(56) References Cited

U.S. PATENT DOCUMENTS

| | | | |
|---|---|---|---|
| 3,348,236 | A | 10/1967 | Copeland |
| 3,378,004 | A | 4/1968 | Claycomb et al. |
| 3,449,761 | A | 6/1969 | Long |
| 3,477,424 | A | 11/1969 | Tracy |
| 3,587,577 | A | 6/1971 | Solyanka et al. |
| 3,610,323 | A | 10/1971 | Troyer |
| 3,648,289 | A | 3/1972 | Moreland |
| 3,738,367 | A | 6/1973 | Hardy |
| 3,786,809 | A | 1/1974 | Kitrilakis |
| 3,839,621 | A | 10/1974 | Hariu |
| 3,892,225 | A | 7/1975 | Twose |
| 3,905,367 | A | 9/1975 | Dapcich |
| 3,908,655 | A | 9/1975 | Lund |
| 4,067,064 | A | 1/1978 | Cerniway et al. |
| 4,074,369 | A | 2/1978 | Harmon |
| 4,108,146 | A | 8/1978 | Golden |
| 4,114,620 | A | 9/1978 | Moore et al. |
| 4,139,004 | A | 2/1979 | Gonzalez, Jr. |
| 4,149,529 | A | 4/1979 | Copeland et al. |
| 4,149,541 | A | 4/1979 | Gammons et al. |
| 4,167,932 | A | 9/1979 | Zebuhr |
| 4,172,495 | A | 10/1979 | Zebuhr et al. |
| 4,194,247 | A | 3/1980 | Melander |
| 4,224,941 | A | 9/1980 | Stivala |
| 4,237,877 | A | 12/1980 | Boehler |
| 4,286,439 | A | 9/1981 | Pasternack |
| 4,294,225 | A | 10/1981 | Mayo |
| 4,353,359 | A | 10/1982 | Milbauer |
| 4,390,997 | A | 7/1983 | Hinz et al. |
| 4,398,535 | A | 8/1983 | Guibert |
| 4,418,745 | A | 12/1983 | Roehr |
| 4,425,916 | A | 1/1984 | Bowen |
| 4,523,594 | A | 6/1985 | Kuznetz |
| 4,566,455 | A | 1/1986 | Kramer |
| 4,572,188 | A | 2/1986 | Augustine et al. |
| 4,575,097 | A | 3/1986 | Brannigan et al. |
| 4,691,762 | A | 9/1987 | Elkins et al. |
| 4,738,119 | A | 4/1988 | Zafred |
| 4,747,408 | A | 5/1988 | Chuan-Chih |
| 4,753,242 | A | 6/1988 | Saggers |
| 4,770,169 | A | 9/1988 | Schmoegner et al. |
| 4,781,193 | A | 11/1988 | Pagden |
| 4,844,072 | A | 7/1989 | French et al. |
| 4,869,250 | A | 9/1989 | Bitterly |
| 4,886,063 | A | 12/1989 | Crews |
| 4,920,963 | A | 5/1990 | Brader |
| 4,969,880 | A | 11/1990 | Zamierowski |
| 4,987,618 | A | 1/1991 | Tolbert |
| 4,998,415 | A | 3/1991 | Larsen |
| 5,062,424 | A | 11/1991 | Hooker |
| 5,097,829 | A | 3/1992 | Quisenberry |
| 5,100,261 | A | 3/1992 | Plemon |
| 5,167,227 | A | 12/1992 | Meserlian |
| 5,168,576 | A | 12/1992 | Krent et al. |
| 5,174,285 | A | 12/1992 | Fontenot |
| 5,230,335 | A | 7/1993 | Johnson, Jr. et al. |
| 5,235,709 | A | 8/1993 | Terlep |
| 5,241,951 | A | 9/1993 | Mason et al. |
| 5,269,369 | A | 12/1993 | Faghri |
| 5,292,347 | A | 3/1994 | Pompei |
| 5,300,105 | A | 4/1994 | Owens |
| D347,491 | S | 5/1994 | Holloway |
| 5,314,455 | A | 5/1994 | Johnson, Jr. et al. |
| 5,330,519 | A | 7/1994 | Mason et al. |
| 5,342,411 | A | 8/1994 | Maxted et al. |
| 5,383,918 | A | 1/1995 | Panetta |
| 5,383,919 | A | 1/1995 | Kelly et al. |
| 5,411,493 | A | 5/1995 | Rodriguez |
| 5,415,222 | A | 5/1995 | Colvin et al. |
| 5,417,720 | A | 5/1995 | Mason |
| 5,423,087 | A | 6/1995 | Krent et al. |
| 5,429,534 | A | 7/1995 | Cano |
| 5,438,707 | A | 8/1995 | Horn |
| 5,449,379 | A | 9/1995 | Hadtke |
| 5,456,701 | A | 10/1995 | Stout |
| 5,470,353 | A | 11/1995 | Jensen |
| 5,486,206 | A | 1/1996 | Avery |
| 5,486,207 | A | 1/1996 | Mahawili |
| 5,496,357 | A | 3/1996 | Jensen et al. |
| 5,507,792 | A | 4/1996 | Mason et al. |
| 5,533,354 | A | 7/1996 | Pirkle |
| 5,562,604 | A | 10/1996 | Yablon et al. |
| 5,603,728 | A | 2/1997 | Pachys |
| 5,609,619 | A | 3/1997 | Pompei |
| 5,634,890 | A | 6/1997 | Morris |
| 5,643,336 | A | 7/1997 | Lopez-Claros |
| 5,683,438 | A | 11/1997 | Grahn |
| 5,697,920 | A | 12/1997 | Gibbons |
| 5,792,216 | A | 8/1998 | Kappel |
| 5,800,483 | A | 9/1998 | Vought |
| 5,871,526 | A | 2/1999 | Gibbs et al. |
| 5,913,885 | A | 6/1999 | Klatz et al. |
| 5,947,914 | A | 9/1999 | Augustine |
| 5,954,680 | A | 9/1999 | Augustine |
| 5,960,469 | A | 10/1999 | Nuckols et al. |
| 5,964,721 | A | 10/1999 | Augustine |
| 5,964,723 | A | 10/1999 | Augustine |
| 5,976,176 | A | 11/1999 | Webb, II |
| 5,986,163 | A | 11/1999 | Augustine |
| 6,030,412 | A | 2/2000 | Klatz et al. |
| 6,045,518 | A | 4/2000 | Augustine |
| 6,050,099 | A | 4/2000 | Lopa et al. |
| 6,086,609 | A | 7/2000 | Buckley |
| 6,109,338 | A | 8/2000 | Butzer |
| 6,113,561 | A | 9/2000 | Augustine |
| 6,113,626 | A | 9/2000 | Clifton et al. |
| 6,117,164 | A | 9/2000 | Gildersleeve et al. |
| 6,126,680 | A | 10/2000 | Wass |
| 6,128,784 | A | 10/2000 | Frank |
| 6,149,674 | A | 11/2000 | Borders |
| 6,156,059 | A | 12/2000 | Olofsson |
| 6,178,562 | B1 | 1/2001 | Elkins |
| 6,197,045 | B1 | 3/2001 | Carson |
| 6,210,427 | B1 | 4/2001 | Augustine et al. |
| 6,213,966 | B1 | 4/2001 | Augustine |
| 6,217,535 | B1 | 4/2001 | Augustine |
| 6,230,501 | B1 | 5/2001 | Bailey et al. |
| 6,238,427 | B1 | 5/2001 | Matta |
| 6,241,697 | B1 | 6/2001 | Augustine |
| 6,241,698 | B1 | 6/2001 | Augustine |
| 6,241,756 | B1 | 6/2001 | Kappel |
| 6,245,094 | B1 | 6/2001 | Pompei |
| 6,245,096 | B1 | 6/2001 | Tomic-Edgar et al. |
| 6,264,622 | B1 | 7/2001 | Augustine |
| 6,276,155 | B2 | 8/2001 | Siman-Tov et al. |
| 6,277,143 | B1 | 8/2001 | Klatz et al. |
| 6,312,453 | B1 | 11/2001 | Stefanile et al. |
| 6,349,412 | B1 | 2/2002 | Dean |
| 6,352,550 | B1 | 3/2002 | Gildersleeve et al. |
| 6,371,976 | B1 | 4/2002 | Vrzalik et al. |
| 6,375,673 | B1 | 4/2002 | Clifton et al. |
| 6,375,674 | B1 | 4/2002 | Carson |
| 6,406,447 | B1 | 6/2002 | Thrash et al. |
| 6,406,448 | B1 | 6/2002 | Augustine |
| 6,407,307 | B1 | 6/2002 | Augustine |
| 6,419,651 | B1 | 7/2002 | Augustine |
| 6,419,691 | B1 | 7/2002 | Hanner |
| 6,423,018 | B1 | 7/2002 | Augustine |
| 6,461,379 | B1 | 10/2002 | Carson et al. |
| 6,500,200 | B1 | 12/2002 | Kushnir |
| 6,520,982 | B1 | 2/2003 | Boynton et al. |
| 6,551,347 | B1 | 4/2003 | Elkins |
| 6,581,400 | B2 | 6/2003 | Augustine et al. |
| 6,602,277 | B2 | 8/2003 | Grahn et al. |
| 6,605,051 | B2 | 8/2003 | Augustine |
| 6,620,187 | B2 | 9/2003 | Carson et al. |
| 6,645,232 | B2 | 11/2003 | Carson |
| 6,648,905 | B2 | 11/2003 | Hoglund et al. |
| 6,656,208 | B2 | 12/2003 | Grahn et al. |
| 6,660,027 | B2 | 12/2003 | Gruszecki et al. |
| 6,669,715 | B2 | 12/2003 | Hoglund et al. |
| 6,692,518 | B2 | 2/2004 | Carson |
| 6,699,267 | B2 | 3/2004 | Voorhees et al. |
| 6,715,309 | B1 * | 4/2004 | Junkins ........................ 62/259.3 |

| | | | |
|---|---|---|---|
| 6,799,063 B2 | 9/2004 | Carson | |
| 6,802,855 B2 | 10/2004 | Ellingboe et al. | |
| 6,818,012 B2 | 11/2004 | Ellingboe | |
| 6,827,728 B2 | 12/2004 | Ellingboe et al. | |
| 6,962,600 B2 | 11/2005 | Lennox et al. | |
| 7,052,509 B2 | 5/2006 | Lennox et al. | |
| 2002/0103520 A1 | 8/2002 | Latham | |
| 2002/0161419 A1 | 10/2002 | Carson et al. | |
| 2003/0163183 A1 | 8/2003 | Carson | |

FOREIGN PATENT DOCUMENTS

| | | |
|---|---|---|
| WO | WO 82/04184 | 12/1982 |
| WO | WO 92/20309 | 11/1992 |
| WO | WO 98/16176 | 4/1998 |
| WO | WO 2006/110405 | 10/2006 |

OTHER PUBLICATIONS

International Search Report from Intl. Appl. No. PCT/US06/12561, mailed Apr. 23, 2007.

Supplementary European Search Report, from EP Appl. No. 03 79 6381, mailed Aug. 31, 2007.

Tooley et al., Head Cooling with Mild Systemic Hypothermia in Anesthetized Piglets is Neuroprotective, Annals of Neurology 53(1):65-72 (2003).

Tooley et al., "Significant Selective Head Cooling Can Be Maintained Long-Term After Global Hypoxia Ischemia in Newborn Piglets," Pediatrics 109(4):643-649 (2002).

* cited by examiner

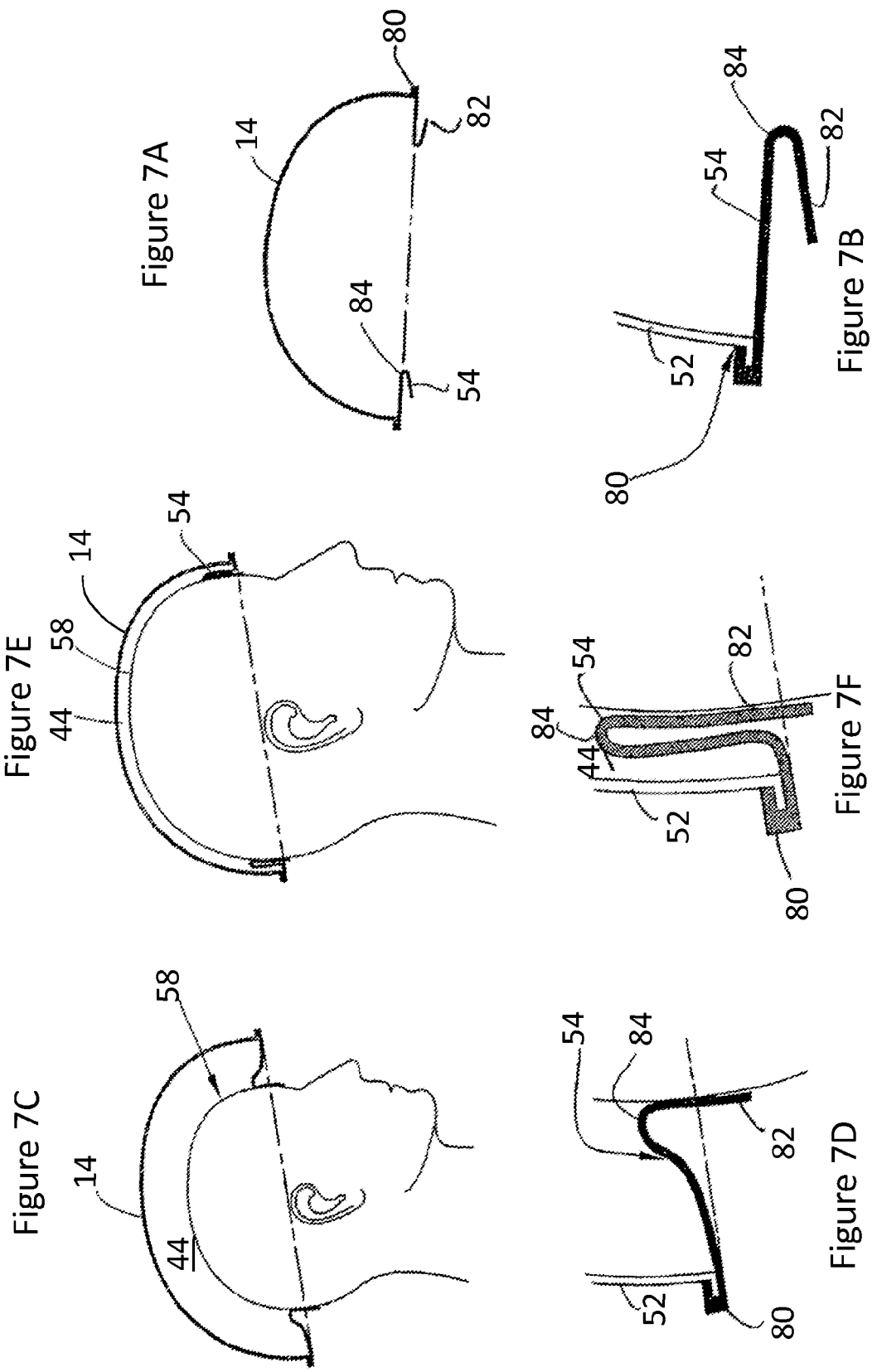

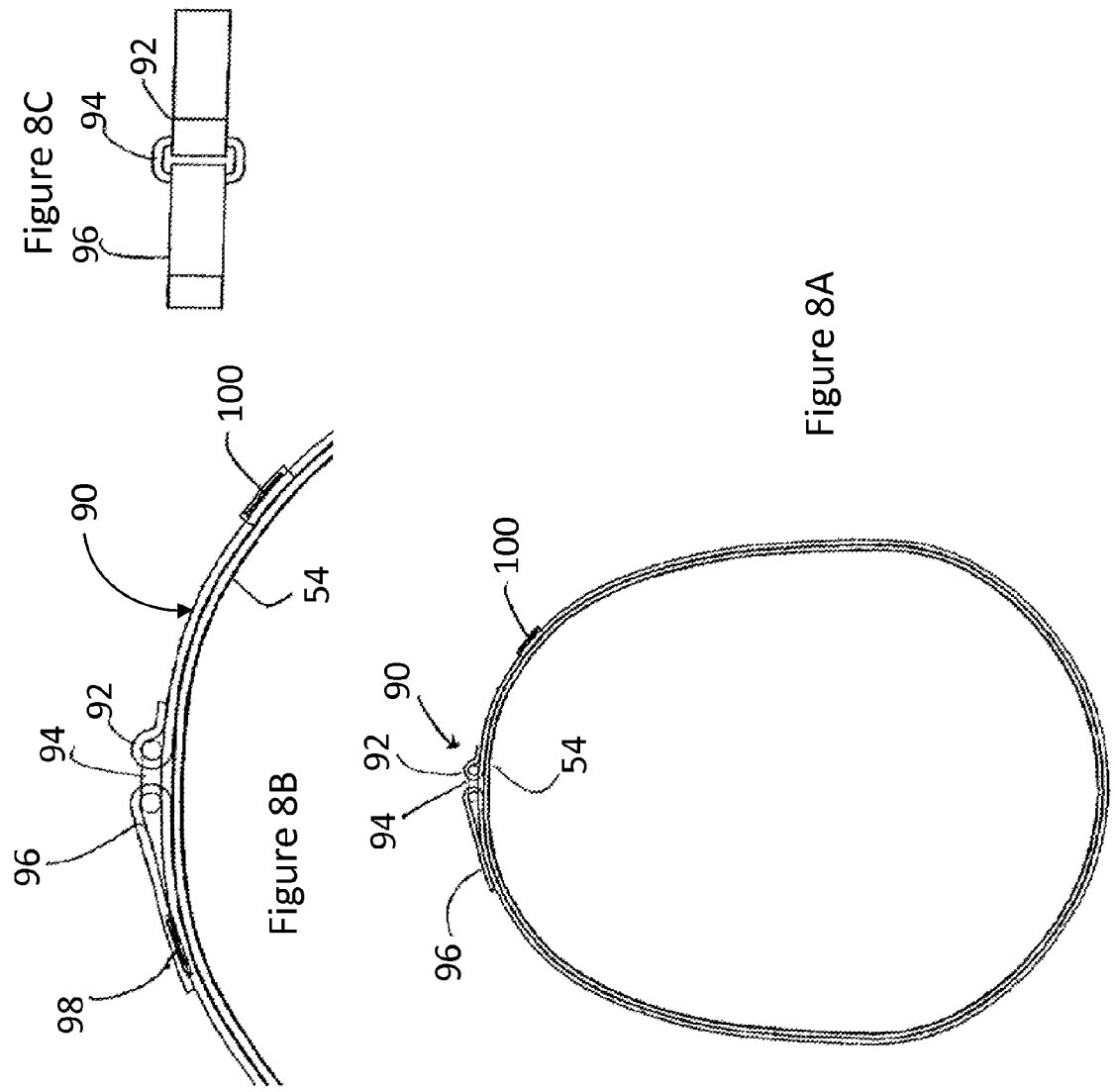

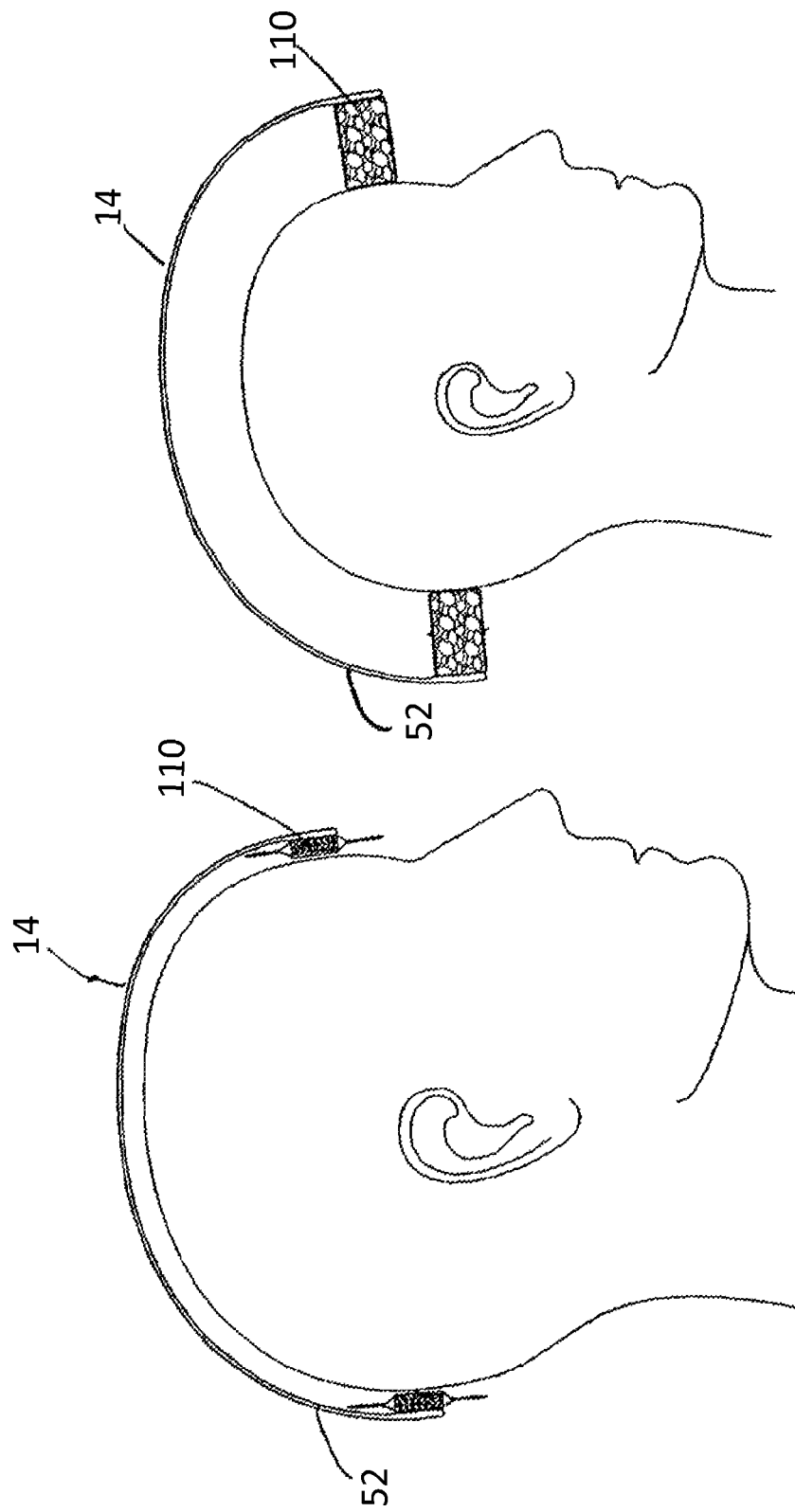

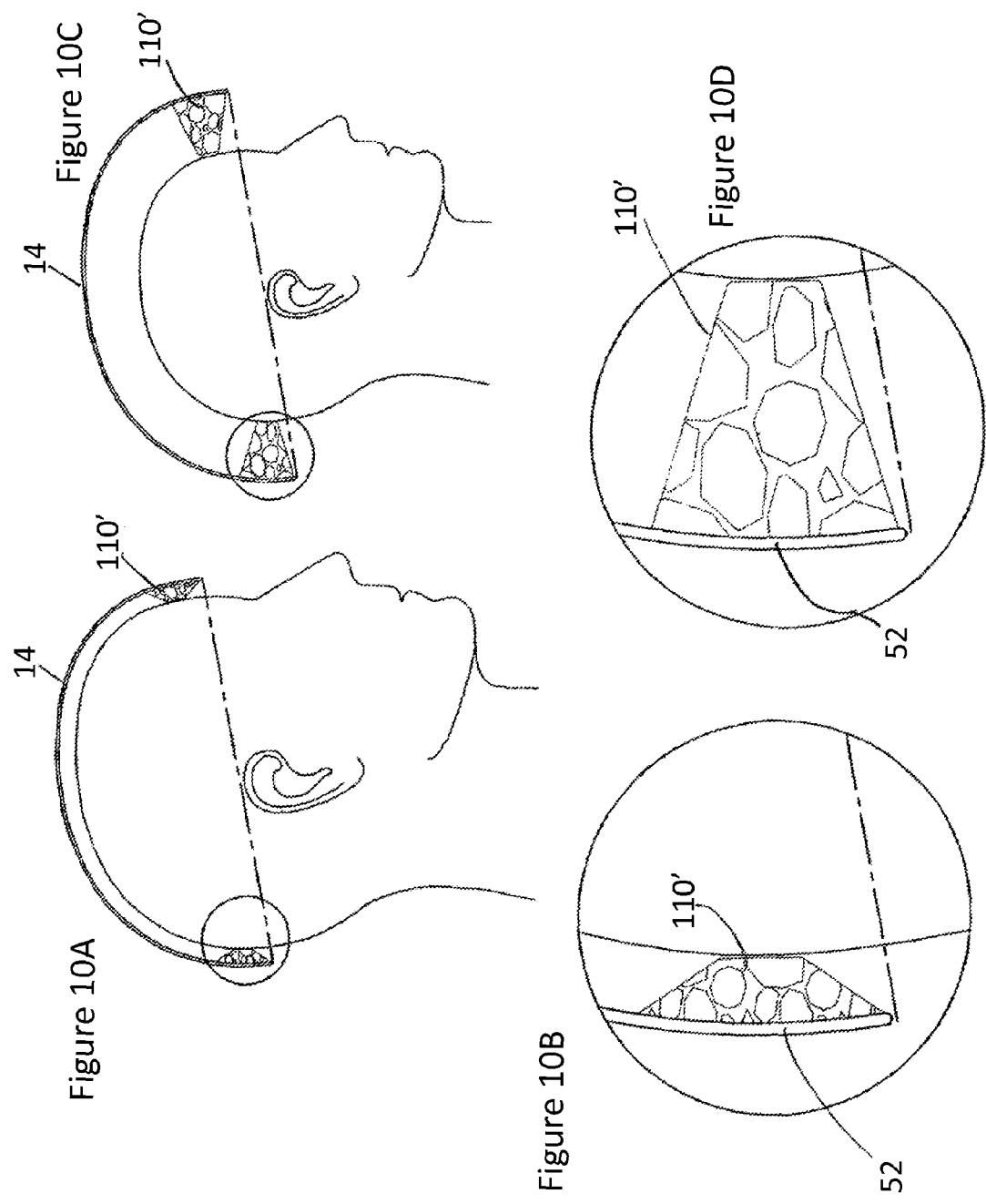

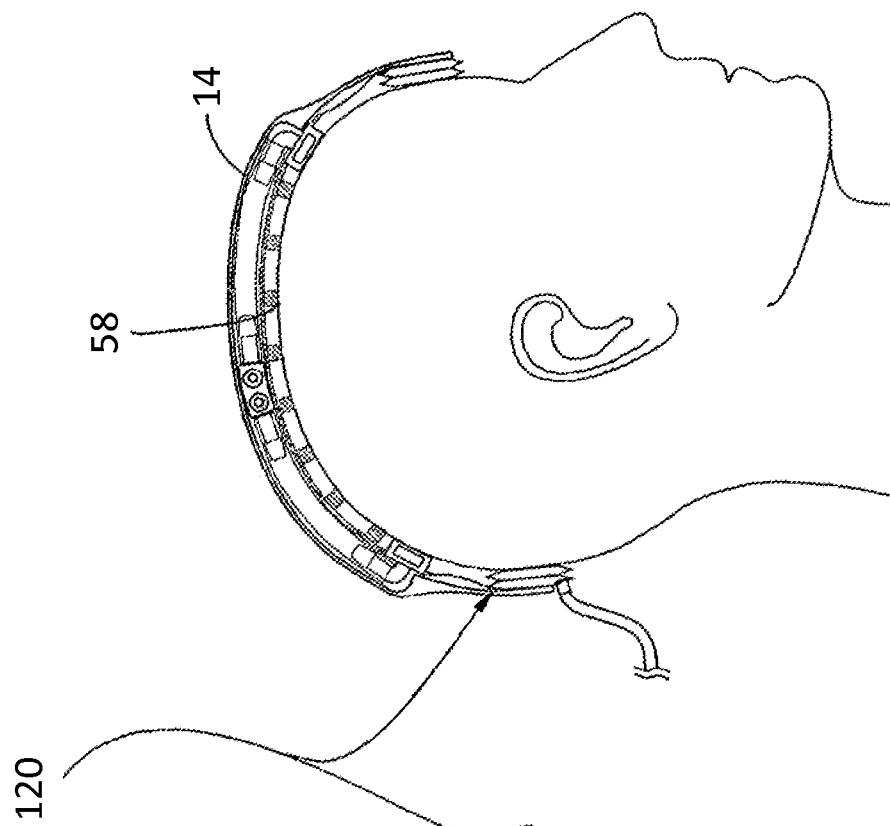
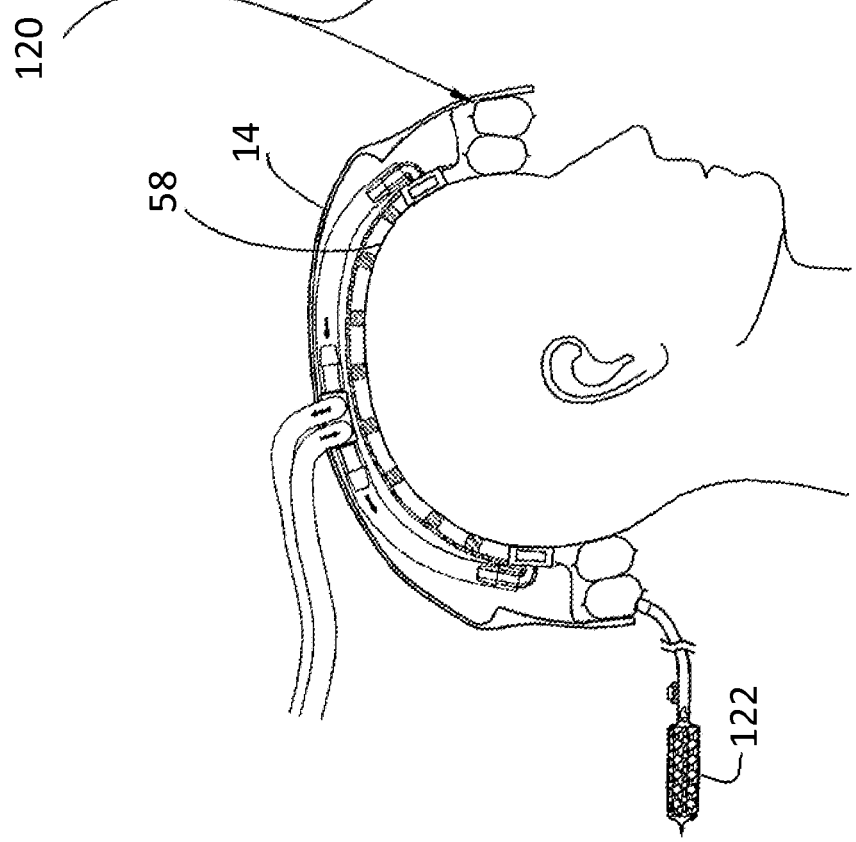
Figure 11A
Figure 11B

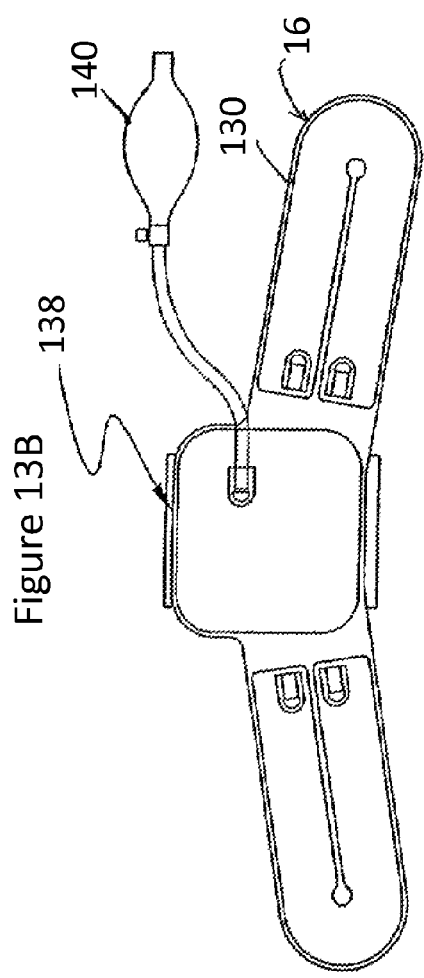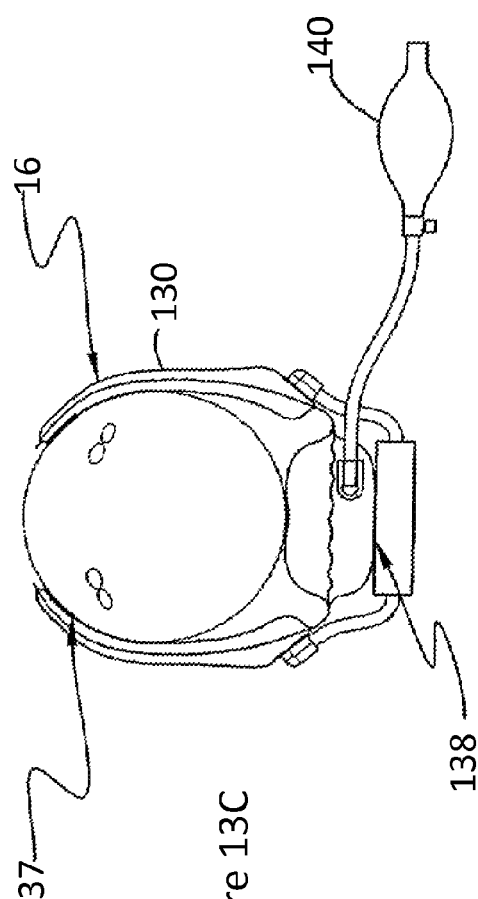

ADJUSTABLE THERMAL CAP

CROSS REFERENCE TO RELATED APPLICATIONS

The present application claims the benefit of a U.S. Provisional Patent Application bearing Ser. No. 60/852,600, filed Oct. 18, 2006, entitled "Adjustable Cooling Cap." The entire contents of the provisional patent application are hereby incorporated by reference herein.

The present application is related to a copending PCT International Patent Application, bearing International Application No. PCT/U.S.2006/012561 and having International Filing Date Apr. 3, 2006; which claims the benefit of U.S. Provisional Patent Application Ser. No. 60/669,336, filed Apr. 7, 2005. These applications are hereby incorporated herein by reference in their entirety.

FIELD OF THE APPLICATION

The present application generally relates to a method and apparatus for heat transfer with a patient, and more particularly to a method and apparatus for cooling a tissue region of interest.

BACKGROUND OF THE APPLICATION

Patients that suffer from stroke, cardiac arrest, or head trauma, as well as patients that have undergone invasive brain or vascular surgery, are at risk for ischemic injury which can occur when an organ does not receive a sufficient supply of oxygen. For example, in the case where a patient suffers from a stroke, a clot blocks the blood supply to a portion of the patient's brain. As a result, the patient can experience a critical rise in intra-cranial pressure, brain cell death, and a loss of brain function.

To help minimize ischemic injury after such a traumatic event, systemic hypothermia can be induced in the patient. The effectiveness of systemic hypothermia therapy is a function of several factors including, for example, the level of cooling of the patient (between temperatures of approximately 30° C. and 35° C.), the amount of time that elapses between an original insult, such as cardiac arrest or heart attack, and achievement of protective levels of hypothermia, and the duration of the hypothermic state.

Systemic hypothermia has historically been applied to a patient by immersion of the patient's body in a cool bath where the depth and duration of hypothermia is limited by the patient's ability to tolerate the therapy. Currently, there are several conventional systemic hypothermia systems available. Such conventional systems include pads having fluid circulation channels disposed within the inner walls of the pads. The pads can be applied to a patient's body and cooled water can be circulated through the pads to cause a thermal exchange between the patient and the pad to induce systemic hypothermia in the patient.

Attempts have also been made to induce hypothermia in a patient by local cooling the surface of the patient's head. For example, certain head-cooling devices include a head cap with a gel-filled liner. Prior to use, the head cap is placed into a freezer to reduce the temperature of the gel. During use, the cap can be placed on the head of a patient such that thermal exchange occurs between the chilled liner and the patient's head to locally induce hypothermia in the head of the patient. However, the presence of hair and/or air pockets between the scalp of the patient and the liner walls can act as a thermal insulator and can minimize the effectiveness of the heat transfer between the patient's scalp and the cap.

There is a need for improved hypothermia devices that provide direct contact between a cooling fluid and a patient's scalp to induce local hypothermia within a patient.

SUMMARY OF THE INVENTION

Embodiments of the present invention relate to an adjustable thermal cap that can fit a variety of head sizes. In many embodiments described herein, the adjustable cap is described as an adjustable cooling cap or a head-cooling device. It is understood, however, that such adjustable caps can be readily configured to be warming caps, as is within the knowledge of one skilled in the art.

One embodiment is directed to a head-cooling device for inducing hypothermia. The device includes an outer covering adapted to at least partially surround a patient's head. The device can also include an adjustable head support structure disposed between the outer covering and the patient's head. The adjustable head support structure can define, at least in part, a fluid circulation space into which a cooling fluid can be introduced to contact the patient's head. The adjustable head support can be configured to fit different head sizes. The adjustable head support can include at least one sizing layer such that a number of sizing layers, which can optionally interlock in a stacked manner, can be selected to accommodate a patient's head size. One or more of the sizing layers can include a protrusion to define, at least in part, a volume of the fluid circulation space. The adjustable head support can also be coupled to a moveable band support that is adjustable to a size of the patient's head, and can alter the volume of the fluid circulation space. The device can also have at least one inlet for introducing the cooling fluid into the fluid circulation space, and at least one fluid outlet for withdrawing the cooling fluid.

In some embodiments, a head-cooling device can include a sealing member for maintaining fluid within the fluid circulation space. The sealing member can be configured to press upon the head with a pressure of at least approximately 90 mmHg. In some aspects, the sealing member can be configured, for example as a flexible membrane, to extend from a periphery of the outer covering toward the fluid circulation space along a surface of the patient's head, or from the periphery away from the outer covering along a head's surface. The sealing member can also be configured to maintain a folded configuration. The sealing member can also include a foam ring disposed within the periphery of the outer covering, and/or at least one inflatable bladder configured to expand and seal against the patient's head. A sealing member can also include a belting system for sealing the perimeter of the head-cooling device against the patient's head.

The cooling cap can also operate in conjunction with a cooling neck collar. The neck collar can include two fluid circulation chambers that can contact the neck of the patient and provide cooling to blood flowing through the carotid arteries and jugular veins of a patient (e.g., in the vicinity of the chambers). The neck collar can also include an inflatable bladder or bolster that can provide support the back of the patient's neck during operation.

BRIEF DESCRIPTION OF THE DRAWINGS

The invention will be more fully understood from the following detailed description taken in conjunction with the accompanying drawings, in which:

FIG. 7A is a side sectional view of an embodiment of a head covering device where the sealing mechanism is formed as a folded band;

FIG. 7B is a side sectional view of the sealing mechanism of FIG. 7A;

FIG. 7C illustrates the positioning of the sealing mechanism of FIG. 7A relative to the head of a patient when multiple sizing layers are disposed within the head covering device;

FIG. 7D is a side sectional view of the sealing band of FIG. 7C;

FIG. 7E illustrates the positioning of the sealing mechanism of FIG. 7A relative to the head of a patient when a single sizing layer is disposed within the head covering device;

FIG. 7F is a side sectional view of the sealing band of FIG. 7E;

FIG. 8A illustrates an embodiment of a sealing mechanism having a flexible membrane and a belting system disposed about the outer periphery of the head covering device;

FIG. 8B illustrates a portion of the belting system of FIG. 8A;

FIG. 8C illustrates a top view of the belting system of FIG. 8B;

FIG. 9A illustrates another embodiment of the sealing mechanism configured as a foam element disposed about the inner periphery of the head covering device, the foam element being compressed to fit a relatively large sized head;

FIG. 9B illustrates a configuration of the foam element of FIG. 9A wherein the element is expanded to fit a relatively small sized head;

FIG. 10A illustrates an alternate embodiment of the head covering device of FIG. 9A where the foam element has a wedge shaped profile;

FIG. 10B illustrates a sectional view of the foam element of FIG. 10A;

FIG. 10C illustrates an alternate embodiment of the head covering device of FIG. 9B where the foam element has a wedge shaped profile;

FIG. 10D illustrates a sectional view of the foam element of FIG. 10C;

FIG. 11A is a side sectional view of a head covering device having a flexible membrane and sealing mechanism configured as a set of inflatable bladders;

FIG. 11B illustrates the head covering device of FIG. 11A having the inflatable bladders in a relatively collapsed state;

FIG. 13B is a top view of the body covering device of FIG. 13A;

FIG. 13C is a side sectional view of the body covering device of FIG. 13A; and

DETAILED DESCRIPTION

The present invention relates to a "one size fits all" thermal cap that can fit a variety of head sizes. The cap includes a shell having a fluid inlet and outlet, removable sizing layers disposed within the shell, and an elastomeric member disposed about the periphery of the shell. Depending upon the size of a patient's head, sizing layers can either be added to or removed from the outer shell (e.g., for smaller or larger heads, respectively) to maintain a fluid circulation space between the head and the rigid shell and allow substantially even distribution of a thermal fluid about the scalp of the patient during operation. The elastomeric member can seal the periphery of the cap to the patient's head and prevent leakage of the thermal fluid from the cap. General features of thermal devices for heating and cooling the head of a subject are revealed in pending a U.S. patent application bearing Ser. No. 11/284,114, filed Nov. 21, 2005 entitled "Method and Device for Rapidly Inducing and Then Maintaining Hypothermia." All the material in the previously mentioned patent application is hereby incorporated herein by reference.

As noted earlier, many embodiments herein are described as adjustable cooling caps. It is understood, however, that such caps can be readily configured to be warming caps, or caps that are designed to maintain a particular temperature or temperature range. Accordingly, the scope of the present invention includes adjustable caps that are designed for any number of thermal conditions (e.g., cooling or warming).

Figure 1:
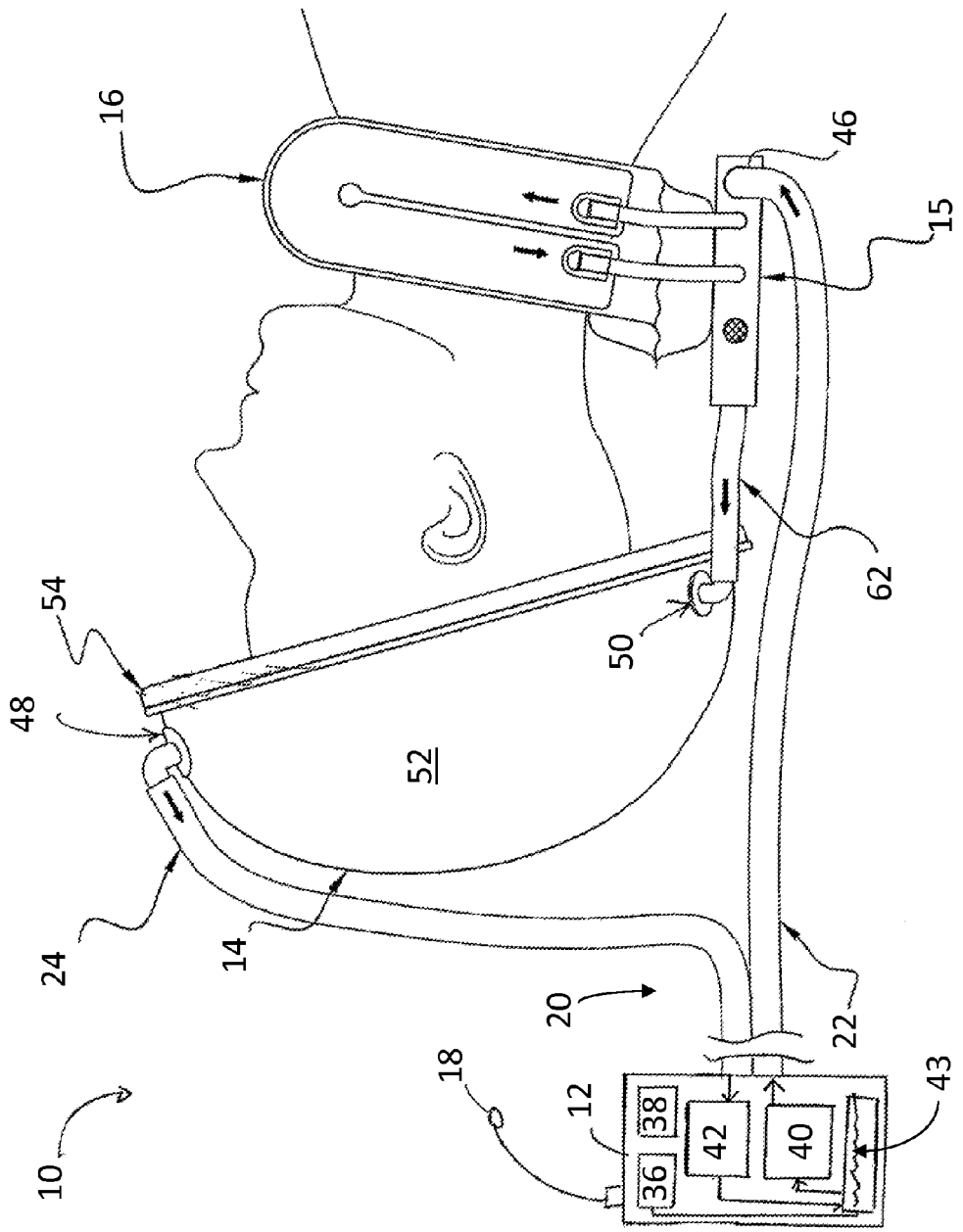
FIG. 1 is a side view of an embodiment of a head covering device and a body covering device of a thermal regulation system.

FIG. 1 illustrates an embodiment of a thermal regulation system 10 that is generally operable to induce localized hypothermia in a patient. The thermal regulation system 10 includes a console 12 having a reservoir 13 that contains a thermal exchange fluid 43, such as cooling fluid. The system 10 also includes a head covering device or cap 14 and a body covering device 16 coupled to the console 12 via a manifold 15. In one embodiment, the head covering device 14, manifold 15, and the body covering device 16 can be removeably connected to console 12 by an umbilical 20 having a fluid inlet tube 22 coupled to the manifold 15 and a fluid outlet tube 24 coupled to the head cap 14. In use, the head cap 14 and body covering device 16 can be placed in contact with a patient's head and body, respectively. The console 12 can then circulate the cooling fluid 43 through the head cap 14 and the body covering device 16 via pumps 40, 42 to cause the devices 14, 16 to exchange thermal energy with, and induce hypothermia in, the patient.

The console 12 can include a temperature sensor 18 that is configured to attach onto an outer surface or within a natural orifice of a patient's body to measure the temperature of the patient during operation of the thermal regulation system 10. For example, in one embodiment, the temperature sensor 18 is an esophageal temperature sensor configured to insert within an esophagus of a patient to measure core body temperature. In another embodiment, the body temperature sensor 18 is a bladder temperature sensor or a tympanic temperature sensor configured to insert within a bladder or ear, respectively, of the patient.

In one embodiment, the temperature of the cooling fluid 43 can be adjusted by the console 12 to control the temperature of the patient's body. For example, the console 12 can include a thermal adjustment device 36, such as a refrigeration mechanism, that can regulate the temperature of the cooling fluid 43 carried by the reservoir 13. During operation, the thermal adjustment device 36 can increase or decrease the temperature of the cooling fluid 43 held in the reservoir 13 in response to signals received from the body temperature sensor 18. The thermally adjusted cooling fluid can then be delivered to the head cap 14 and the body covering device 16 to adjust the patient's body temperature.

In another embodiment, the console 12 can also include a flow rate adjustment mechanism 38 to adjust the flow of thermal regulation fluid from console 12 to the head covering device 14 and the body covering device 16. For example, flow rate adjustment mechanism 38 can be a computerized controller (e.g., a processor and memory) that forms a feedback loop with the body temperature sensor 18 and the pumps 40, 42. In response to the signals received from the body temperature sensor 18, the controller 38 can adjust the rate of delivery of cooling fluid 43 by the pumps 40, 42 to the head cap 14 and the body covering device 16. During operation, an increase in the rate of delivery of cooling fluid 43 to the head cap 14 and the body covering device 16 can increase the cooling rate in the patient while a decrease in the rate of delivery of cooling fluid 43 can decrease the cooling rate in the patient.

As indicated above, the console pumps 40, 42 are operable to deliver cooling fluid 43 to the head cap 14 and body cooling device 16 and to generate a negative gage pressure within the head cap 14. For example, the pumps 40, 42 can be disposed between the reservoir 13 and the head cap 14 and body cooling device 16 such that the first pump 40 couples to an inlet 46 of the manifold 15, which in turn couples to an inlet 50 of the head cap 14, and the second pump 42 couples to an outlet 48 of the head cap 14. In use, the first pump 40 delivers thermal exchange fluid from a reservoir 44 to the manifold 15 at a first flow rate. The manifold 15, in turn, transmits the fluid 43 at the first flow rate to the body cooling device 16 and to the head cap 14 via cap inlet 50. The second pump 42 removes fluid from the head cap 14 at a second flow rate, which is less than the first flow rate. The difference in flow rates between the first pump 40 and the second pump 42 allows the cooling fluid 43 to flow through the head cap 14 at a relatively high flow rate, such as between approximately 3 liters/min and 6 liters/min, thereby providing thermal exchange between the patient's head and the thermal exchange fluid. Also, the difference in flow rates between the first pump 40 and the second pump 42 creates a slightly negative pressure within a fluid circulation space between the head cap and the patient's head. Such negative pressure can help to maintain the cooling fluid 43 substantially within the head cap 14 and minimize leakage of the fluid 43 past the cap's perimeter.

Figure 13A:
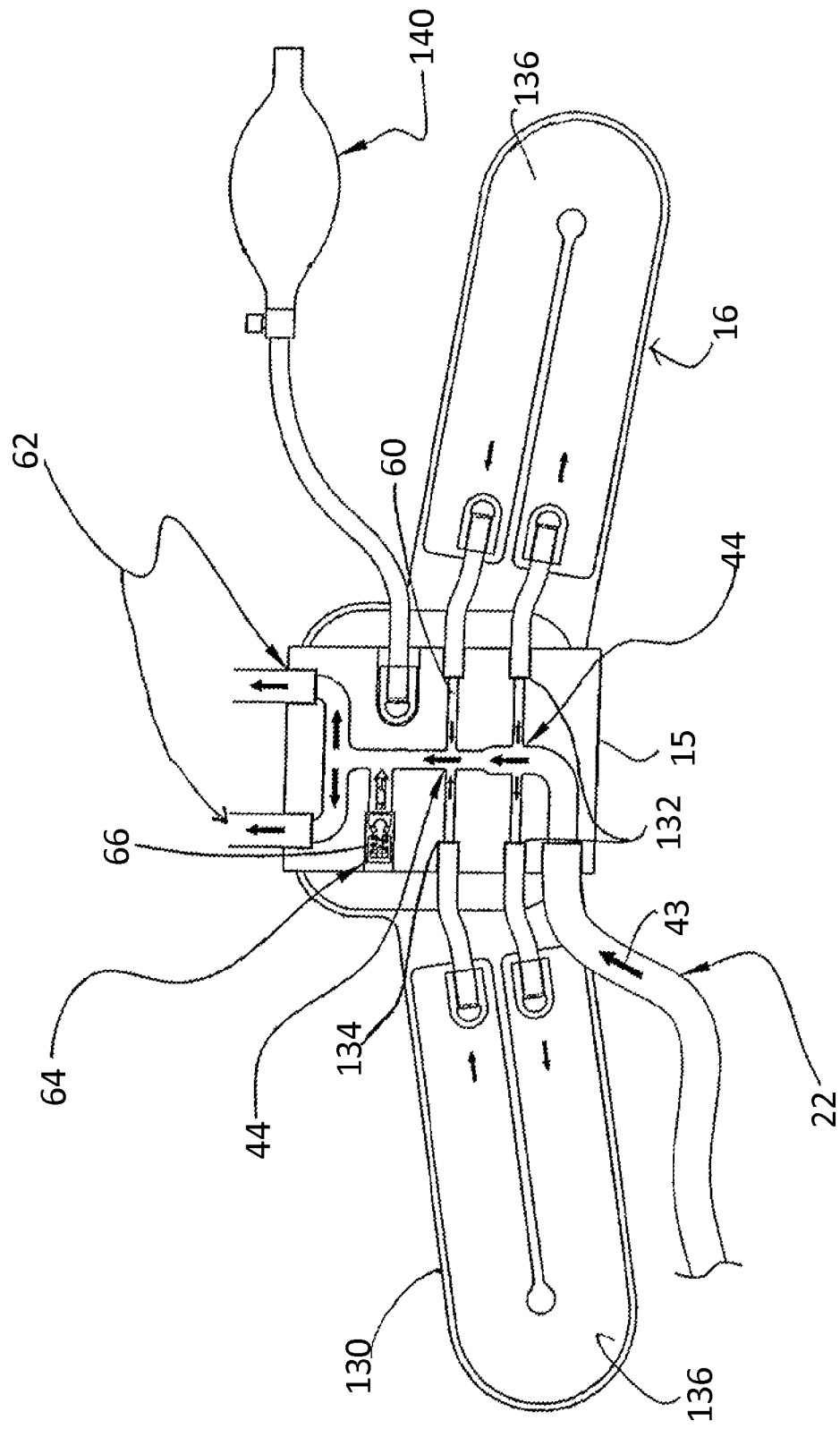
FIG. 13A is a sectional top view of the body covering device of FIG. 1.

The manifold 15 is operable to distribute fluid 43 from the console to both the head cap 14 and body cooling device 16. For example, as shown in FIG. 13A, the manifold 15 receives the cooling fluid 43 from the console 12 though the fluid inlet tube 22. The manifold 15 can then circulate the cooling fluid 43 through the body covering device 16 via branches 60 and deliver the fluid 43 into the head cap 14 via branches 62.

In one embodiment, the manifold 15 can include a vent port 64 that allows air to flow into the fluid circulation space 44 to maintain a slightly negative pressure therein, as caused by the out flow from the fluid outlet 48 being greater that the inflow from the fluid inlet 50 of the head cap 14 (see FIGS. 1 and 13A). Additionally, the air can create turbulence within the fluid circulation space 44 and, as a result, can minimize stagnation of fluid flow or boundary layer effects relative to an inner wall of the head cap 14 and can increase the rate of induction and depth of hypothermia in the patient. While the vent 64 can have a variety of configurations, in one embodiment the vent 64 includes a check valve 66 that allows air to flow into the branches 62 of the manifold 15 and that limits or prevents fluid 43 from flowing out from the manifold 15 via the vent port 64.

Figure 2:
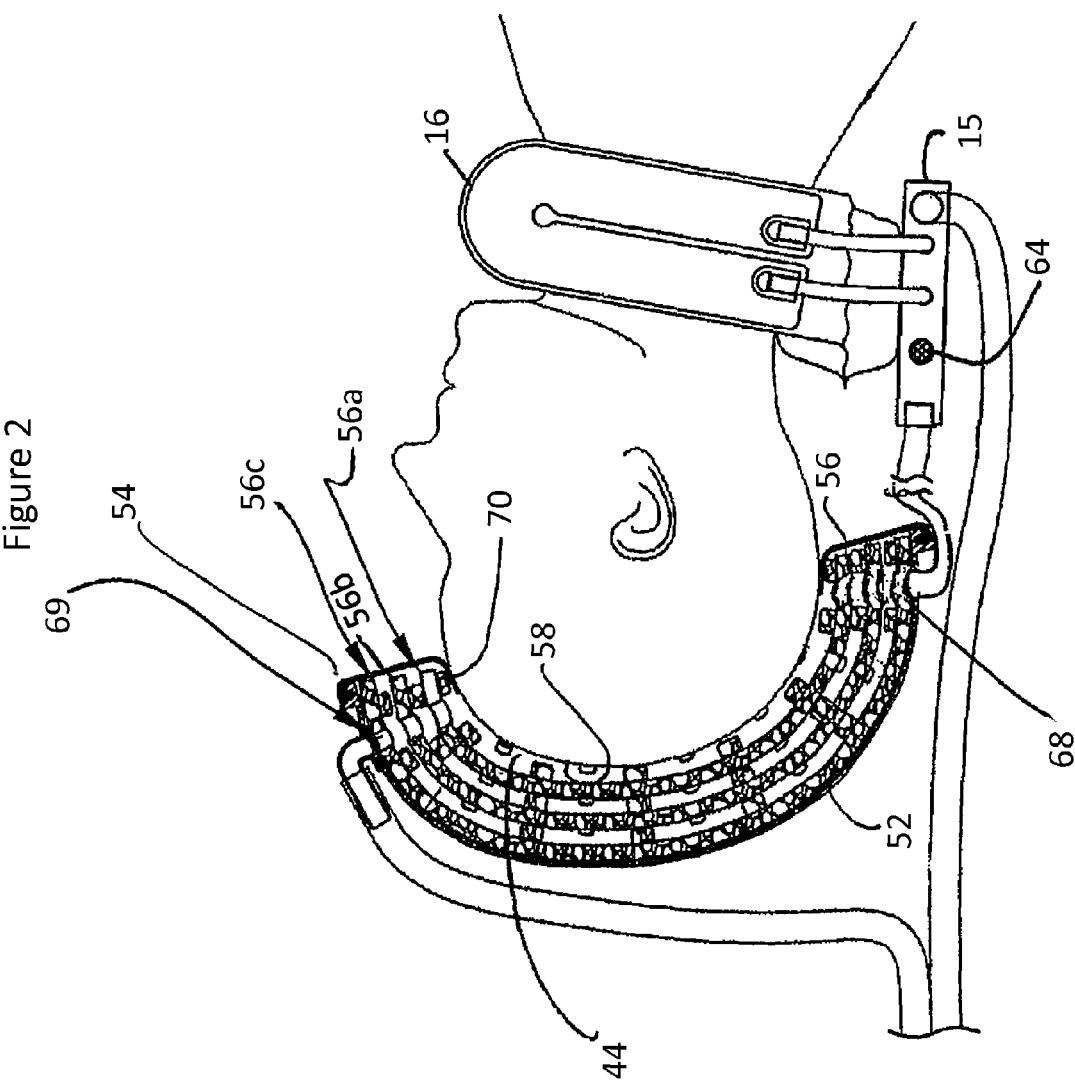
FIG. 2 is a side sectional view of an embodiment of the head covering device shown in FIG. 1 having multiple sizing layers disposed between an outer shell of the head covering device and a patients' scalp.
Figure 3:
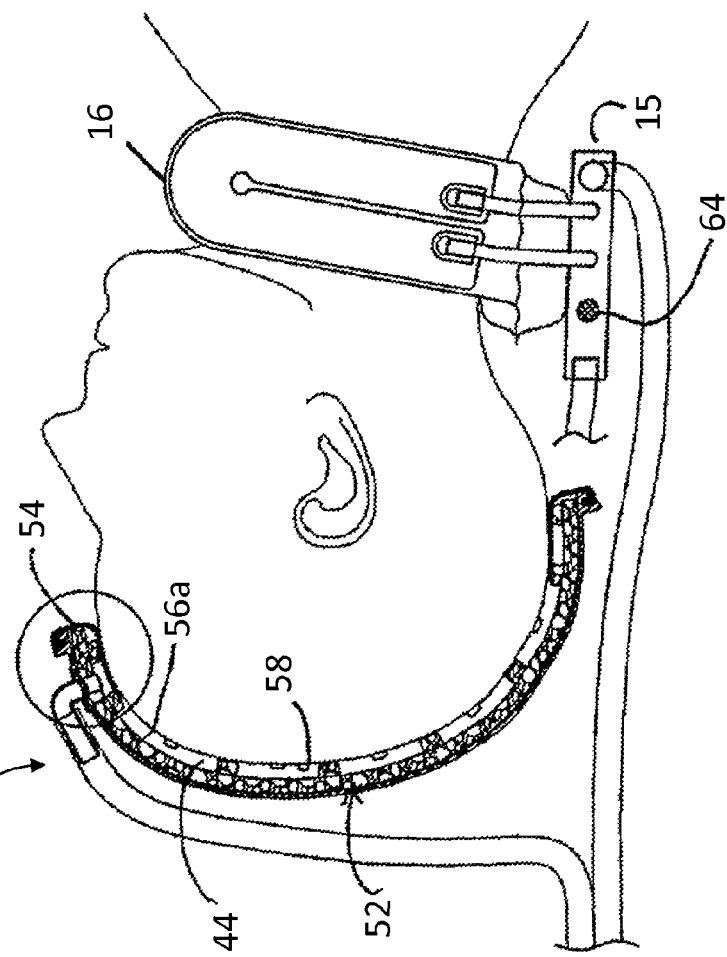
FIG. 3 is a side sectional view of another embodiment of the head covering device shown in FIG. 1 having a single sizing layer disposed between an outer shell of the head covering device and a patients' scalp.

The head cap 14 is adapted to fit a variety of head sizes. For example, as illustrated in FIGS. 1-3, the head cap 14 includes a shell 52 formed from a relatively rigid material, such as a polycarbonate material, and a sealing member 54 disposed about a periphery of the head cap 14. The shell 52 and sealing member 54, along with a patient's scalp 58, define a fluid circulation space 44. The head cap 14 can also include one or more sizing layers 56 disposed between the shell 52 and the patient's scalp 58 within the fluid circulation space 44.

Each sizing layer 56 can be formed from a substantially compliant material that forms a cushion between the patient's head and the shell 52. For example, the sizing layers 56 can be formed from a foam material and, in particular, formed from an open-cell foam material that allows the cooling fluid 43 to flow through the sizing layer 56 between the shell 52 and the patient's scalp 56. Alternatively, or in addition, each layer can include a series of aligned channels to facilitate fluid circulation with the head cap.

The sizing layers 56 are provided to adjust an inner volume of the shell 52 to allow the head cap 14 to fit or substantially conform to a geometry of a patient's head. The number of sizing layers 56 placed within the shell 52 depends upon the size of the patient's head. For example, as indicated in FIG. 2, in the case where a patient has a relatively small sized head, a number of sizing layers 56, such as layers 56a, 56b, and 56c can be stacked within the shell 52 and, as indicated in FIG. 3, in the case where a patient has a relatively large sized head, a single sizing layer 56a can be inserted within the shell 52. As a patient's head is inserted within the head cap 14, the presence of one or more sizing layers can secure the patient's head within the head cap 14 to limit motion of the patient's head relative to the shell 52.

Each sizing layer 56 can include fluid inlet and outlet openings 68, 69 that align with the fluid inlet 50 and outlet 48 of the shell 52 and that are configured to direct cooling fluid 43 to the patient's scalp 58 during operation. As illustrated in FIG. 2, when multiple sizing layers 56 are stacked within the shell 52, the inlet and outlet openings 68, 69 of each sizing layer 56 align with each other in a concentric manner. In such an arrangement, during operation, the openings 68, 69 direct the cooling fluid 43 toward the patient's scalp.

The sizing layers 56, in conjunction with the shell 52 and the sealing element 54, also define and maintain a fluid circulation space 44 with the patient's scalp 56. For example, during operation, the pumps 40, 42 generate a negative pressure within the head cap 14 that can force the shell 52 toward the patient's scalp 58 and can minimize the volume of the fluid circulation space available for cooling fluid circulation. To minimize a reduction in the volume of the fluid circulation space during operation, the sizing layers 56 can include one or more protrusions 70 that extend radially toward the scalp 58 of the patient. In such a configuration, during operation, as the negative pressure forces the shell 52 toward the patient's head, the protrusions 70 maintain the sizing layers 56 in a spaced apart relationship with the patient and thereby maintain the fluid circulation space 44 to allow substantially even distribution of the cooling fluid 43 about the scalp 58 of the patient.

Figure 5:
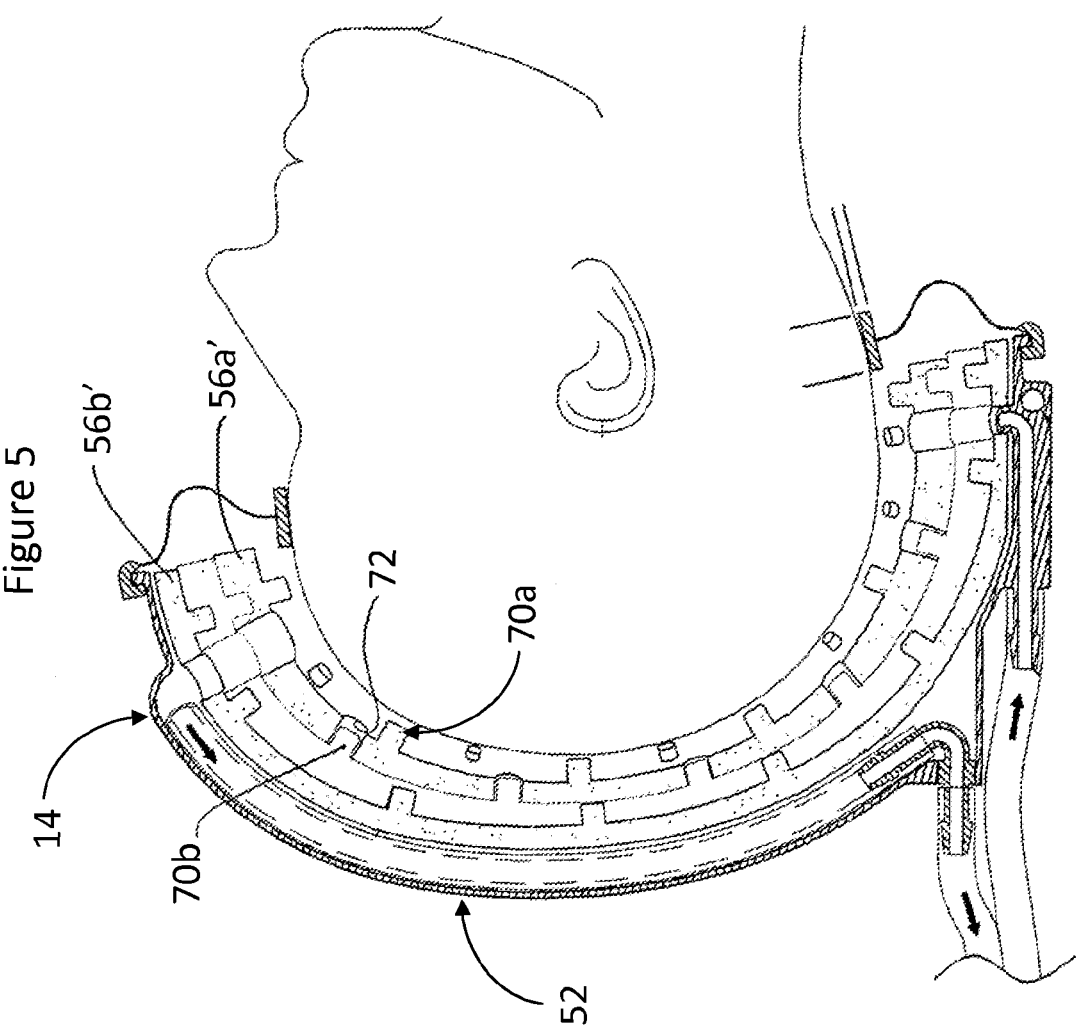
FIG. 5 illustrates another embodiment of the head covering device of FIG. 1.
Figure 6C:
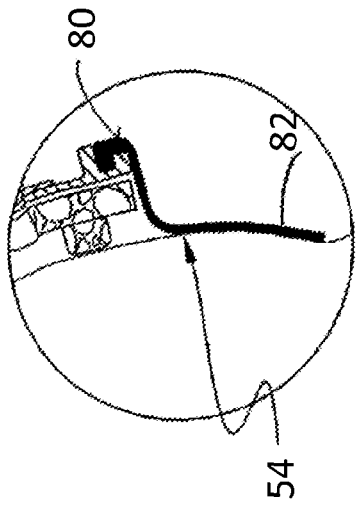
FIG. 6C illustrates another configuration of the sealing mechanism of FIG. 6A when a single sizing layer is disposed within the head covering device.
Figure 6D:
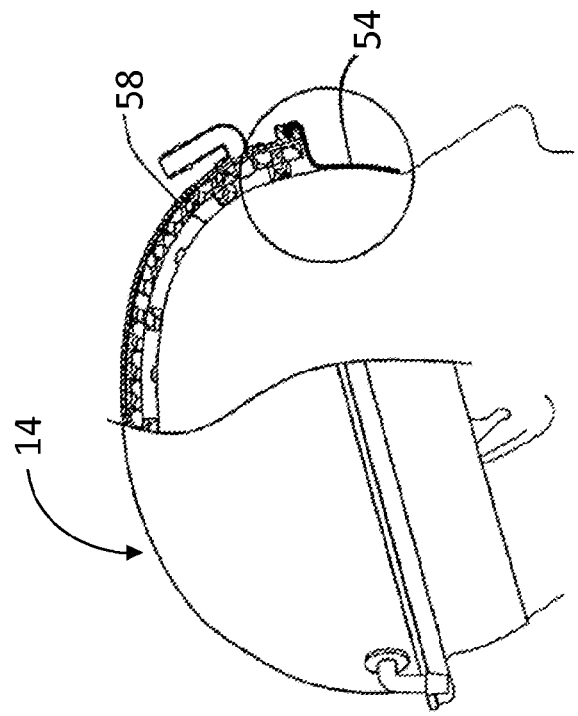
FIG. 6D illustrates a relation between the sealing mechanism of FIG. 6C and the head of a patient when a single sizing layer is disposed within the head covering device.
Figure 6A:
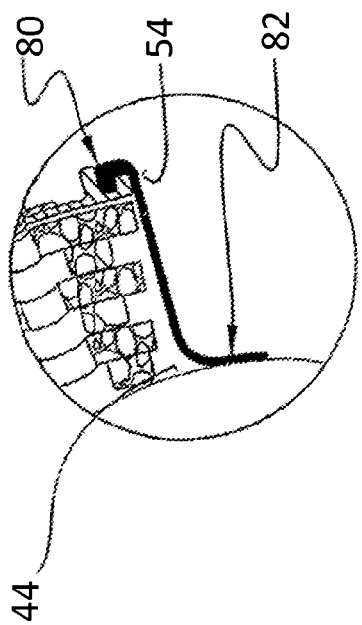
FIG. 6A illustrates a configuration of a sealing mechanism of the head covering device where the sealing mechanism extends radially outward relative to the head covering device when placed on a patient's head.
Figure 6B:
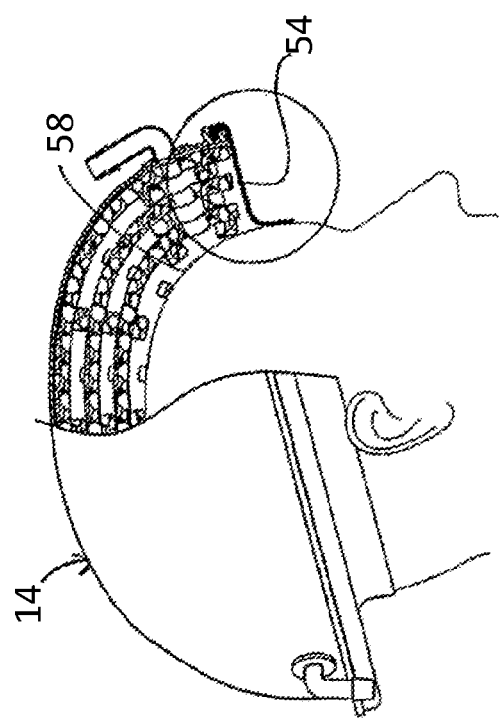
FIG. 6B illustrates a relation between the sealing mechanism of FIG. 6A and the head of a patient when multiple sizing layers are disposed within the head covering device.

In one embodiment, the protrusions 70 of adjacent can also operate to interlock adjacent sizing layers 56 together to secure the sizing layers within the head cap 14. As indicated in FIG. 5, each sizing layer 56a' and 56b' includes protrusions 70a, 70b that extend radially toward the patient's scalp from a first surface and the second sizing layer 56a' includes openings 72 formed within a second surface. For example, after the first sizing layer 56b' has been disposed within the shell 52, when the second sizing layer 56a' is inserted therein, the protrusions 70b of the first sizing layer 56b' insert within the openings 72 of the second sizing layer 56a' to form a friction fit between the adjacent layers 56a', 56b'. Interlocking of the layers 56a', 56b' can maintain their relative positioning within the head cap 14 during use.

Returning to FIG. 1, the sealing member 54, such as formed from an elastomeric material, is configured to allow a single sized head cap 14 to be applied to a variety of head sizes and to seal the cap 14 to the patient's head, thereby maintaining cooling fluid 43 within the fluid circulation space 44 of the head cap 14 during operation. In one embodiment, the sealing member 54 applies a pressure of at least approximately 90 mmHg to the patient's head. Such pressure provides an adequate seal between the head cap 14 and the patient's head and allows blood to flow through the patient's tissue in contact with the sealing member 54.

Figure 4:
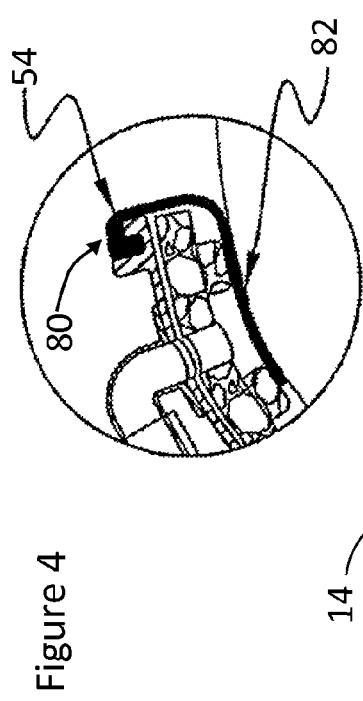
FIG. 4 illustrates a configuration of a sealing mechanism of the head covering device where the sealing mechanism extends radially inward relative to the head covering device when placed on a patient's head.

FIG. 4 illustrates an embodiment of the sealing member 54 having a first end 80 coupled about a periphery of the shell 52 and a second end 82 that extends from the shell 52 and that is adapted to conform to a geometry of a patient's head. In use, the sealing member 54 can be extended or compressed in a variety of ways to seal the head cap 14 to the patient's head.

FIGS. 2-4 illustrate one configuration of the sealing member 54 when the head cap 14 is placed on the patient's head. As shown, the second end 82 of the sealing member 54 extends over the rim of the cap 14 and into the fluid circulation space 44 defined by the cap 14 to provide sealing between the patient's head and the cap. In another configuration of the sealing member 54 as illustrated in FIGS. 6A-6D, when the head cap 14 is placed on the patient's head, the second end 82 of the sealing member 54 can extend radially away from the periphery of the cap 14 to form a seal with the patient's head. In such a configuration, because the sealing member 54 does not substantially extend into the fluid circulation space 44, the sealing member 54 allows cooling fluid 43 to contact the patient's scalp 58 about the periphery of the device 14.

In yet another configuration of the sealing member 54 as illustrated in FIGS. 7A-7F, the sealing member 54 can include a fold portion 84 disposed between the first end 80 and the second end 82 of the sealing member 54. In such a configuration, when the cap 14 is applied to a patient's head, the fold portion 84 extends within the fluid circulation space 44 while the second end 82 extends radially away from the periphery of the cap 14. In use, the fold portion 84 can help to absorb a sealing pressure applied to the patient's head by the sealing member 54 to maintain the pressure below approximately 90 mm Hg.

In one embodiment, the sealing member 54 can include an adjustable belting system to seal the perimeter of the cap 14 against a patient's head. For example, FIGS. 8A-8C illustrate a belting system 90 disposed about the sealing member 54 at the periphery of the head cap 14. The belting system 90 can include a first end 92 coupled to a belt loop 94 and a second end 96 threaded through the belt loop 94 and that can adjustably fasten to itself via a fastening mechanism 98, such as VELCRO for example. In use, the second end 96 can be advanced through the belt loop 94 to tighten the belt system 90 and the sealing member against a patient's head. In one embodiment, the belting system includes a pressure gauge 100 that provides an indication of the amount of pressure generated by the belting system 90 and sealing member 54 against the patient's head against. As such, the pressure gauge can indicate when the pressure approaches or exceeds approximately 90 mm Hg.

While the sealing member 54 can be formed from an elastomeric material, other materials can be used as well. For example, FIGS. 9A-10D illustrate the sealing member 54 configured as a foam ring 110 disposed within an inner periphery of the head cap 14. In use, when the head cap 14 is placed on a patient's head, the head can compress the foam ring 110 radially toward an inner surface of the shell 52 to form a seal between the head and the head cap 14. The degree of compression of the foam ring 110 is dependent upon the size of the patients head. For example, the foam ring 110 illustrated in FIG. 9A is compressed to a greater degree than the foam ring 110 illustrated in 9B since the patient's head in FIG. 9A is larger than the patient's head in FIG. 9B.

The foam ring 110 can have a variety of geometric configurations. As shown in FIGS. 9A and 9B, the foam ring 110 can have a generally rectangular sectional geometric configuration. In another embodiment, as shown in FIGS. 10A-10D, the foam ring 110' can have a generally trapazoidal sectional geometric configuration.

FIGS. 11A and 11B illustrate an embodiment of the sealing member 54 configured as an one or more inflatable bladders 120 disposed within the inner periphery of the head cap 14. When inflated via a pressure bulb 122, the bladders 120 can expand between an inner wall of the cap 14 and the patient's scalp 58 to seal the head cap 14 against the patient's head.

Figure 12:
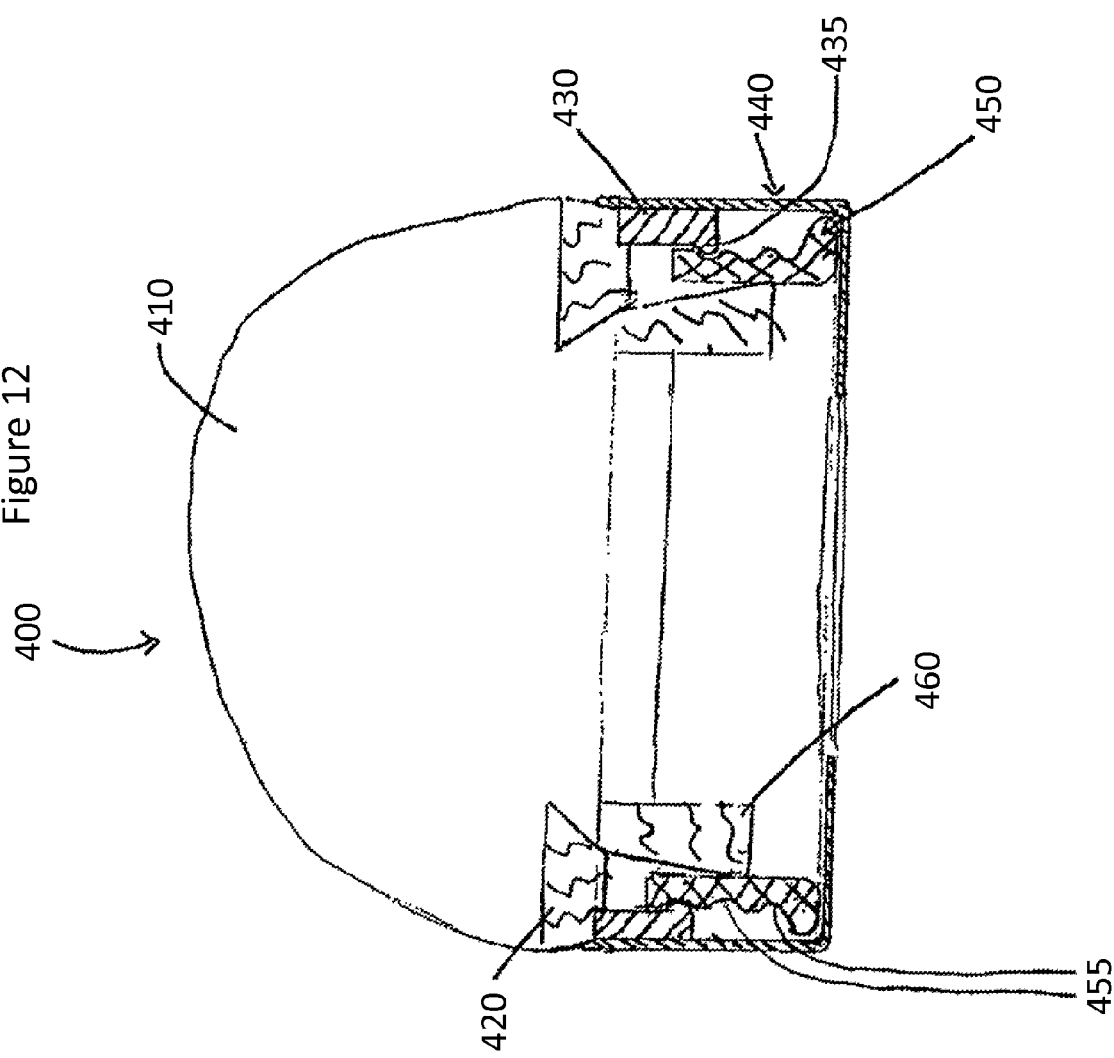
FIG. 12 is a side view of a head covering device having an adjustable head support.

FIG. 12 illustrates another embodiment of a head cooling device 400 that is adjustable to a user's head size. The head cooling device 400 includes an outer layer 410, which can be embodied as a rigid dome shell. The device 400 includes an adjustable head support 460 that is configured to adjustably move up and down, i.e., toward and away from the outer layer 410, respectively. The head support 460 is configured to contact a user's head to support the head cooling device 400. The head support 460 can be made from a deformable material such as foam. A head support can be embodied in a number of shapes and configurations including as a multiplicity of supports. The head support 460 can be adjusted to contact a smaller circumference head as the head support 460 is moved up. The head support 460 can be coupled to a band support 450, which can be configured to move the head support 460 up or down. In the embodiment shown in FIG. 12, the band support 450 includes a number of sizing grooves 455 that can interlock with a protrusion 435 of band interlock 430, providing a plurality of vertical positions for the band support 450, and thus the foam support 460. As the foam support 460 moves up, foam wedge 420 can be shaped to push foam support 460 radially inward. Thus, as the head support 460 moves up, the corresponding inward movement of the support 460 accommodates a smaller circumference head. As well, the upward movement of the support 460 can result in a smaller volume within the cap for circulating fluid. Therefore, the volume of contact fluid in the cap can be correspondingly adjusted. A soft sealing member 430 can be affixed to the periphery of the outer layer 410 for providing a sealing mechanism for sealing cooling fluid from leaking out of the outer layer 410. The sealing member 430 can be adjusted to accommodate the moveable position of the band support 450. Potential sealing members can include any of the sealing members discussed herein for sealing a cooling device to the body.

Returning to FIG. 1, as described above, the body covering device 16 can be placed in contact with a patient body. As the console 12 circulates cooling fluid 43 through the body covering device 16, the device 16 can exchange thermal energy with, and induce hypothermia in, the patient. In one embodiment, the body covering device 16 is configured as a collar 130, an embodiment of which is illustrated in FIGS. 13A-13C. Generally, the collar 130 provides thermal exchange with the arteries and veins within neck area of a patient. The collar 130 includes fluid inlets 132 and fluid outlets 134 in fluid communication with the manifold 15 and fluid circulation spaces 136 disposed between each fluid inlet 130 and the fluid outlet 132. The collar 130 can be secured to the patient's neck via an adhesive tape 137. The collar 130 can also include a bladder 138 that can be inflated with a pressure bulb 140. When inflated, the bladder 138 provides support to a patient's neck.

Embodiments of the collar 130 can minimize the amount of pressure placed on a patient's airway when the collar 130 is placed on the neck of the patient. The collar 130, thereby, minimizes or prevents choking of the patient.

Figure 14:
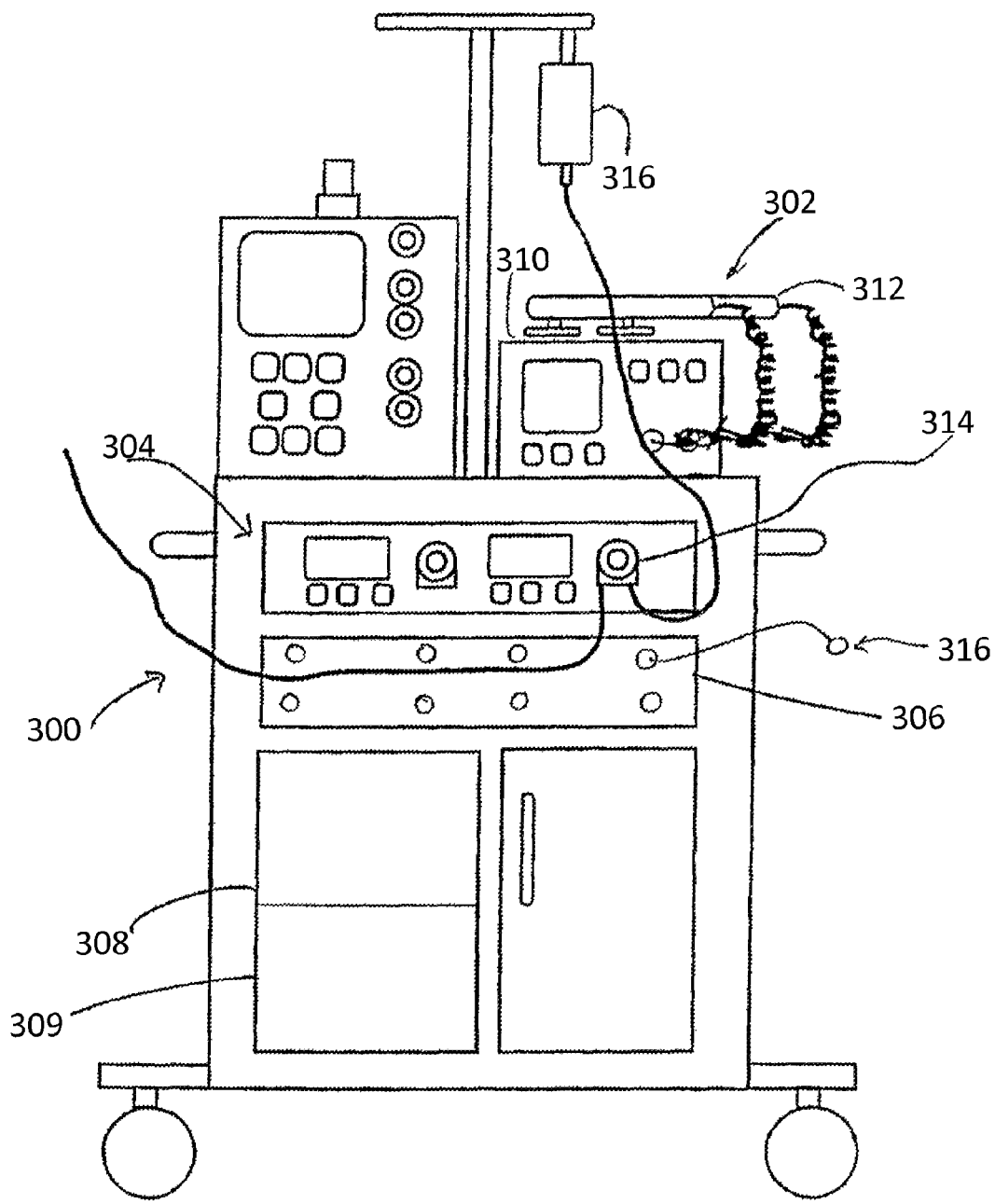
FIG. 14 illustrates a resuscitation system that includes a thermal regulation system, such as shown in FIG. 1.

In certain cases, a patient may need to undergo a resuscitation procedure in conjunction with hypothermia therapy. FIG. 14 illustrates an embodiment of the thermal regulation system 10 forming part of a resuscitation system 300 various mechanisms necessary to or used in a resuscitation process. For example, the resuscitation system 300 can include a defibrillation apparatus 302, a fluid treatment apparatus 304, a physiologic monitoring apparatus 306, a ventilator 308, and a chest compression apparatus 309.

The defibrillation apparatus 302 can include a defibrillator 310 and defibrillator electrodes 312. After applying the defibrillation electrodes 312 to a patient and activating the defibrillator 310, an electrical current is provided to the patient's heart to restore a normal rhythm thereto.

The fluid treatment apparatus 304 can include a fluid infusion pump 314 that provides metered infusion of fluids into the patient. The pump 314 can deliver the fluids, such as a Ringer's solution, from a fluid bag 316 to the patient to maintain a hydration level of the patient.

In another arrangement the pump 314 can deliver a fluid medicament from the fluid bag 316 to the patient to aid in patient resuscitation.

The physiological monitor 306 and sensor 316 can detect a physiologic state of a patient and can adjust delivery of thermal exchange fluid 43 from the console 12 to the head or body cooling devices 14, 16 to adjust or maintain the patient's body temperature based upon the detected physiologic state. For example, the physiological monitor 180 can be an electrocardiogram (ECG) sensor, an electroencephalogram (EEG) sensor, a heart monitoring sensor, a temperature sensor, or a pulse oximetry sensor.

The ventilator 308 can couple to a patient airway and provide oxygen and other gasses to the patient during a resuscitation procedure. The chest compression apparatus 309 can couple to the chest of the patient and can operate in conjunction with the ventilator to cyclically compress the patient's chest and aid in the resuscitation of the patient.

In one embodiment, the thermal regulation system 10 can be used in conjunction with neurological monitoring equipment. For example, the thermal regulation system 10 can be used in conjunction with an intracranial pressure monitoring device. In use, the intracranial pressure monitoring device can measure, for example, a pressure of the cerebrospinal fluid within a patient's brain ventricle. Based upon the pressure measured by the pressure monitoring device, the thermal regulation device 10 can adjust the temperature of the fluid within the ventricle by adjusting the temperature of the thermal regulation fluid 43 delivered to the head cap 14 or body cooling device 16 or by adjusting a rate of delivery of the thermal regulation fluid 43 to the head cap 14 or body cooling device 16.

One skilled in the art will appreciate further features and advantages of the invention based on the above-described embodiments. For example, though the embodiments discussed herein are directed to a head-cooling device, it is understood that such devices can also be employed to provide heating to a patient's head if needed. Accordingly, the invention is not to be limited by what has been particularly shown and described, except as indicated by the appended claims. All publications and references cited herein are expressly incorporated by reference in their entirety.

What is claimed is:

1. A head-cooling device for inducing hypothermia comprising:
    an outer covering adapted to at least partially surround a patient's head;
    an adjustable head support structure adapted to form a fluid circulation space between the outer covering and the patient's head into which a cooling fluid can be introduced, the adjustable head support capable of being configured to fit different head sizes and further comprising a sealing member for maintaining fluid within the fluid circulation space, including at least one inflatable bladder configured to expand and seal against the patient's head;
    at least one inlet for introducing the cooling fluid into the fluid circulation space; and
    at least one fluid outlet for withdrawing the cooling fluid.

2. The head-cooling device of claim 1, wherein the adjustable head support includes at least one sizing layer such that a number of sizing layers can be selected to accommodate a patient's head size.

3. The head-cooling device of claim 2, wherein each sizing layer is configured to interlock with another sizing layer in a stack manner.

4. The head-cooling device of claim 2, wherein at least one sizing layer includes a protrusion to define a volume of the fluid circulation space.

5. The head-cooling device of claim 1, wherein the sealing member is configured to press upon the head with a pressure of at least approximately 90 mmHg.

6. The head cooling device of claim 1, wherein the inflatable bladder is disposed within an inner periphery of the head cap and along a surface of the patient's head.

7. The head-cooling device of claim 1, wherein the adjustable head support is coupled to a moveable band support that is adjustable to a size of the patient's head.

8. The head-cooling device of claim 7, wherein the movable band support is configured to adjust a volume of the fluid circulation space.

* * * * *